(12) United States Patent
Liu

(10) Patent No.: US 10,994,154 B2
(45) Date of Patent: May 4, 2021

(54) MEDICAL IMAGE-BASED RADIATION SHIELDING DEVICE AND METHOD THEREOF

(71) Applicant: NEUBORON MEDTECH LTD., Jiangsu (CN)

(72) Inventor: Yuan-hao Liu, Jiangsu (CN)

(73) Assignee: NEUBORON MEDTECH LTD., Nanjing (CN)

( * ) Notice: Subject to any disclaimer, the term of this patent is extended or adjusted under 35 U.S.C. 154(b) by 305 days.

(21) Appl. No.: 16/246,645

(22) Filed: Jan. 14, 2019

(65) Prior Publication Data

US 2019/0143141 A1 May 16, 2019

Related U.S. Application Data

(63) Continuation of application No. PCT/CN2017/092499, filed on Jul. 11, 2017.

(30) Foreign Application Priority Data

Nov. 14, 2016 (CN) .......................... 201611029477.8
Nov. 14, 2016 (CN) .......................... 201621222853.0

(51) Int. Cl.
*A61N 5/10* (2006.01)
*B33Y 30/00* (2015.01)
(Continued)

(52) U.S. Cl.
CPC .................. *A61N 5/10* (2013.01); *A61B 6/10* (2013.01); *B33Y 30/00* (2014.12); *B33Y 50/02* (2014.12);
(Continued)

(58) Field of Classification Search
CPC .... A61N 2005/1076; A61N 2005/1094–1096;
(Continued)

(56) References Cited

U.S. PATENT DOCUMENTS

2013/0043408 A1 2/2013 Claereboudt et al.
2015/0006098 A1* 1/2015 Ju .......................... A61N 5/1075
702/84

(Continued)

FOREIGN PATENT DOCUMENTS

CN 1634620 A 7/2005
CN 106061554 A 10/2016
(Continued)

OTHER PUBLICATIONS

Wei Zou et al., Potential of 3D printing technologies for fabrication of electron bolus and proton compensators, Journal of Applied Clinical Medical Physics, vol. 16, No. 3, 2015.
(Continued)

*Primary Examiner* — Thaddeus B Cox
(74) *Attorney, Agent, or Firm* — Locke Lord LLP; Tim Tingkang Xia, Esq.

(57) ABSTRACT

A medical image-based radiation shielding device and method thereof, which may form a targeted and highly accurate radiation shielding according to individual differences in patients, such as tumor location and size, thereby reduce or avoid radiation from a irradiation apparatus to normal tissues of patients. The shielding device includes a medical image scanning means for scanning an irradiated site of an irradiated subject and outputting medical image voxel data, a data processing and three-dimensional modeling means for establishing a three-dimensional phantom tissue model according to the medical image voxel data and establishing a three-dimensional shield model according to the three-dimensional phantom tissue model; a shield located between the irradiation apparatus and the irradiated site, wherein the shield is formed by printing the three-dimensional shield model data input to a 3D printer.

13 Claims, 2 Drawing Sheets

(51) Int. Cl.
  *B33Y 50/02* (2015.01)
  *B33Y 80/00* (2015.01)
  *B33Y 10/00* (2015.01)
  *A61B 6/10* (2006.01)

(52) U.S. Cl.
  CPC ........ *B33Y 80/00* (2014.12); *A61N 2005/109* (2013.01); *A61N 2005/1076* (2013.01); *A61N 2005/1094* (2013.01); *A61N 2005/1096* (2013.01); *B33Y 10/00* (2014.12)

(58) Field of Classification Search
  CPC .... A61N 2005/1085–1098; A61N 5/10–1084; B33Y 10/00; B33Y 30/00; B33Y 40/00–20; B33Y 50/00–02; B33Y 70/00–10; B33Y 80/00; B33Y 99/00
  See application file for complete search history.

(56) References Cited

U.S. PATENT DOCUMENTS

| | | | |
|---|---|---|---|
| 2015/0094838 A1 | 4/2015 | Mac Laverty | |
| 2016/0256709 A1* | 9/2016 | Robar | G16H 50/30 |
| 2016/0256711 A1 | 9/2016 | Pappas et al. | |
| 2017/0007848 A1* | 1/2017 | Drees | H01J 37/14 |
| 2017/0361535 A1* | 12/2017 | Ju | A61N 5/1077 |
| 2018/0169440 A1 | 6/2018 | Liu et al. | |

FOREIGN PATENT DOCUMENTS

| | | |
|---|---|---|
| EP | 2810693 A2 | 12/2014 |
| EP | 2846694 B1 | 9/2016 |
| JP | 2004233168 A | 8/2004 |
| JP | 2008022920 A | 2/2008 |
| JP | 2013061295 A | 4/2013 |
| RU | 104440 U1 | 5/2011 |
| WO | 2008140486 A2 | 11/2008 |
| WO | 2015077881 A1 | 6/2015 |
| WO | 2015138382 A1 | 9/2015 |

OTHER PUBLICATIONS

International Search Report of PCT/CN2017/092499, dated Sep. 12, 2017.
EPO, "Extended European Search Report for EP Application No. 17870064.7", Munich, Germany, dated Aug. 5, 2019.
Russian Patent Office, "Russian Search Report for Russian Application No. 2019103225/14(005890)", Russia, dated Aug. 27, 2019.

* cited by examiner

MEDICAL IMAGE-BASED RADIATION SHIELDING DEVICE AND METHOD THEREOF

RELATED APPLICATION INFORMATION

This application is a continuation of International Application No. PCT/CN2017/092,499, filed on Jul. 11, 2017, which claims priority to Chinese Patent Application No. 201611029477.8, filed on Nov. 14, 2016; and Chinese Patent Application No. 201621222853.0, filed on Nov. 14, 2016, the disclosures of which are hereby incorporated by reference.

FIELD OF THE DISCLOSURE

One aspect of the present disclosure relates to a radiation shielding device for radiotherapy, in particular to a medical image-based radiation shielding device; and another aspect of the present disclosure relates to a radiation shielding method for radiotherapy, in particular to a medical image-based radiation shielding method.

BACKGROUND OF THE DISCLOSURE

As atomics moves ahead, such radiotherapy as Cobalt-60, linear accelerators and electron beams has been one of major means to cancer therapy. However, conventional photon or electron therapy has been undergone physical restrictions of radioactive rays; for example, many normal tissues on a beam path will be damaged as tumor cells are destroyed. On the other hand, sensitivity of tumor cells to the radioactive rays differs greatly, so in most cases, conventional radiotherapy falls short of treatment effectiveness on radioresistant malignant tumors (such as glioblastoma multiforme and melanoma).

For the purpose of reducing radiation damage to the normal tissue surrounding a tumor site, target therapy in chemotherapy has been employed in the radiotherapy. While for high-radioresistant tumor cells, radiation sources with high RBE (relative biological effectiveness) including such as proton, heavy particle and neutron capture therapy have also developed. Among them, the neutron capture therapy combines the target therapy with the RBE, such as the boron neutron capture therapy (BNCT). By virtue of specific grouping of boronated pharmaceuticals in the tumor cells and precise neutron beam regulation, BNCT is provided as a better cancer therapy choice than conventional radiotherapy.

Various radiations are generated during radiotherapy. For example, neutrons and photons of low-energy to high-energy are generated during boron neutron capture therapy. These radiations may cause different degrees of damage to normal human tissues. Therefore, in the field of radiotherapy, how to reduce radiation pollution to the external environment, medical staff or normal tissues of patients is an extremely important issue while effective treatment is achieved. In the existing radiotherapy equipment, the shielding of radiation is mainly focused on the room where the equipment is placed, the equipment itself, without attention to the radiation from the device outlet to the normal tissues of the patients. Further, it is not possible to form a targeted, highly accurate radiation shielding based on individual differences in the patients, such as tumor location, size, shape, and the like.

Medical image data such as data from Magnetic Resonance Imaging (MRI) or Computed Tomography (CT) can provide detailed tissue geometry information for human internal features, and provide a data foundation for solid modeling of human internal structures. Therefore, it is necessary to propose a medical image-based radiation shielding method and device thereof, which can form a targeted and highly accurate radiation shielding, and reduce or avoid radiation to normal tissues of patients.

The statements in this section merely provide background information related to the present disclosure and may not constitute prior art.

SUMMARY

The present disclosure provides a medical image-based radiation shielding device which may shield normal tissues of an irradiated subject from radiation of an irradiation apparatus. The medical image-based radiation shielding device includes a medical image scanning means, a data processing and three-dimensional modeling means and a shield. The medical image scanning means scans an irradiated site of the irradiated subject and outputs medical image voxel data. The data processing and three-dimensional modeling means establishes a three-dimensional phantom tissue model according to the medical image voxel data, and establishes a three-dimensional shield model according to the three-dimensional phantom tissue model. The shield is formed by printing the three-dimensional shield model data input to a 3D printer, and is located between the irradiation apparatus and the irradiated site.

Implementations of this aspect may include one or more of the following features.

The three-dimensional shield model may be established according to the three-dimensional phantom tissue model, combined with data information of the irradiation apparatus and positional relationship between the irradiation apparatus and the irradiated site.

The material of the shield may include at least one of a material for shielding neutrons and a material for shielding photons, and the shield may be fixed on a surface of the irradiated subject to match surface shape of the irradiated subject. The shield may have a central through hole, and a ratio of a diameter of the central through hole to a maximum size of internal diseased tissues of the irradiated subject in a direction perpendicular to a beam direction may be 1-2, and maximum thickness of the shield may range from 3 to 20 mm, and area of the outer surface of the shield may be in the range from 10 to 200 cm².

Radiation generated by the irradiation apparatus may be attenuated by the shield by ≥50%, and a ratio of radiation depth to normal tissues of the radiation when passing through the shield compared to when not passing through may be ≤50%.

Another aspect of the present disclosure provides a radiotherapy system, which includes an irradiation apparatus and a shield, the irradiation apparatus irradiates an irradiated subject to form an irradiated site; the shield is located between the irradiation apparatus and the irradiated site, and is formed by printing with a 3D printer.

Implementations of this aspect may include one or more of the following features.

The radiotherapy system may further include a three-dimensional image scanning means and a data processing and three-dimensional modeling means, wherein the three-dimensional image scanning means scans the irradiated site and outputs three-dimensional data; the data processing and three-dimensional modeling means establishes a three-dimensional model of the irradiated site according to the three-dimensional data, and establishes a three-dimensional shield model according to the three-dimensional model of the irradiated site; the shield may be formed by printing with a 3D printer, data of the three-dimensional shield model is inputted into the 3D printer.

The radiotherapy system may further include a medical image scanning means and a data processing and three-dimensional modeling means, wherein the medical image scanning means scans the irradiated site and outputs medical image voxel data; the data processing and three-dimensional modeling means establishes a three-dimensional phantom tissue model according to the medical image voxel data, and establishes a three-dimensional shield model according to the three-dimensional phantom tissue model; the shield may be formed by printing with a 3D printer, data of the three-dimensional shield model is inputted into the 3D printer.

The irradiation apparatus may include a radiation generating device, a beam shaping assembly, and a collimator, wherein the radiation generating device is capable of generating radiation, the beam shaping assembly is capable of adjusting beam quality of the radiation generated by the radiation generating device, the collimator is capable of concentrating radiation passing through the beam shaping assembly, and the shield may be located between the collimator and the irradiated site.

The radiotherapy system may be a boron neutron capture therapy system, the irradiated subject may be a cancer patient, and the radiation generating device may be a neutron generating device including an accelerator and a target, wherein the accelerator accelerates charged particles to interact with the target to generate neutrons.

Normal tissues of the patient may receive a radiation dose of less than 18 Gy during the boron neutron capture therapy.

The radiotherapy system may further includes a treatment table, wherein the radiation may pass through the shield and act on diseased tissues of the patient on the treatment table, the shield may be fixed on the surface of the irradiated subject or to the treatment table or the collimator.

A third aspect of the present disclosure provides a medical image-based radiation shielding method, the method includes the following steps: scanning an irradiated site of an irradiated subject by a medical image scanning means, and outputting medical image voxel data of the irradiated site; establishing a three-dimensional phantom tissue model according to the medical image voxel data; establishing a three-dimensional shield model according to data of the three-dimensional phantom tissue model; inputting data of the three-dimensional shield model into a 3D printer to print a shield; and installing and positioning the shield.

Implementations of this aspect may include one or more of the following features.

The step of establishing a three-dimensional shield model according to data of the three-dimensional phantom tissue model may further includes collecting or inputting the data information of the irradiation apparatus and the positional relationship between the irradiation apparatus and the irradiated site, and establishing the three-dimensional shield model in combination with the data of the three-dimensional phantom tissue model, and determining shield location.

In the medical image-based radiation shielding method and device according to the present disclosure, the shield is formed by 3D printing, can be respectively formed according to individual differences of different irradiated subjects, and can rapidly model complex shapes, is more targeted, and has higher precision, and can obtain better radiation shielding effect.

Further areas of applicability will become apparent from the description provided herein. It should be understood that the description and specific examples are intended for purposes of illustration only and are not intended to limit the scope of the present disclosure.

Figure 1:
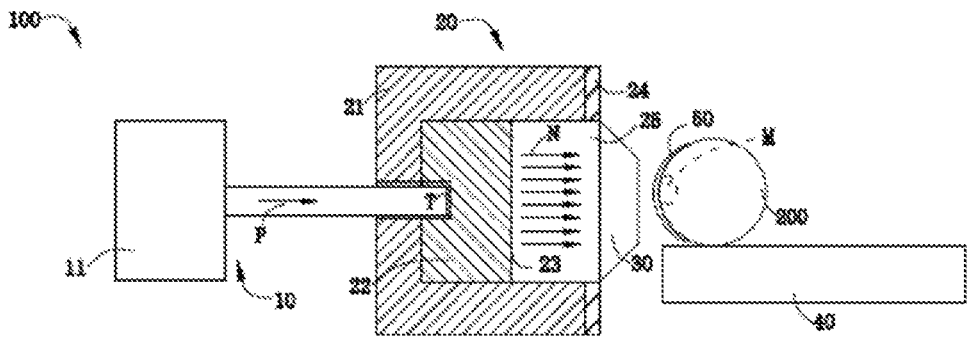
FIG. 1 is a schematic diagram of a boron neutron capture therapy device according to an embodiment of the present disclosure.
Figure 2:
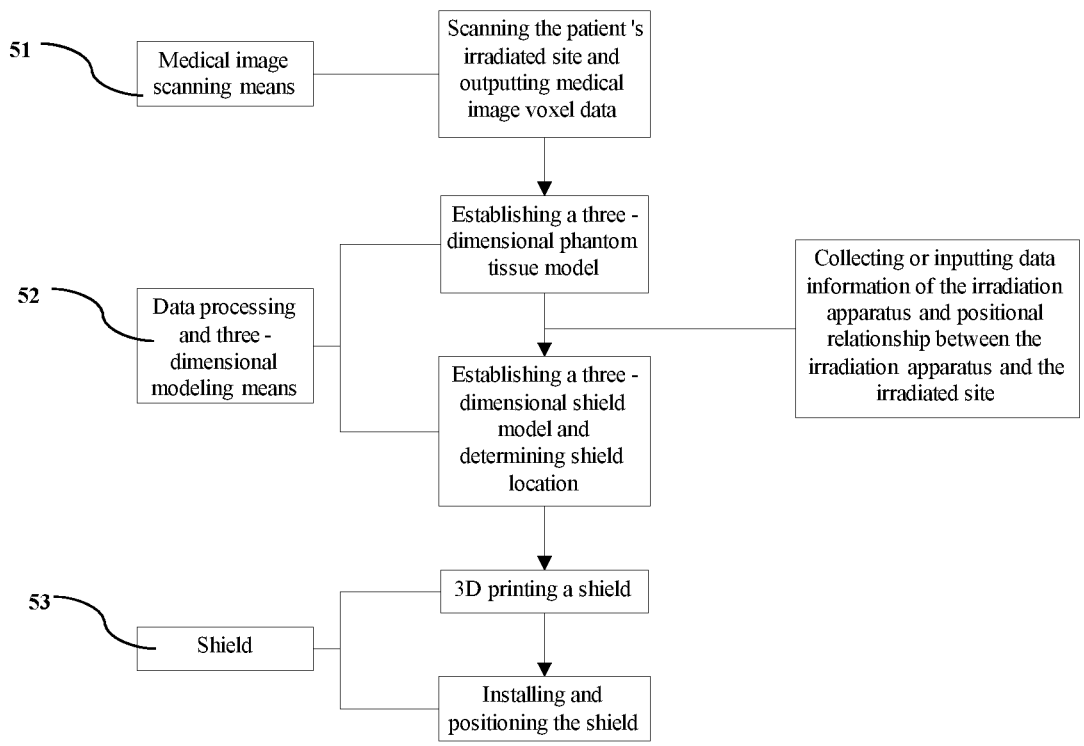
FIG. 2 is a logic block diagram of a medical image-based radiation shielding method in an embodiment of the present disclosure.
Figure 3:
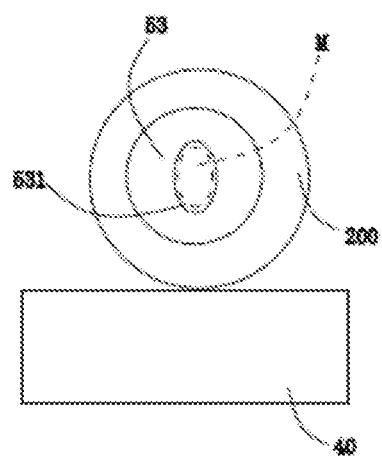
FIG. 3 is a schematic diagram showing the positional relationship between a shield and an irradiated subject according to an embodiment of the present disclosure.

The drawings described herein are for illustrative purposes only of selected embodiments and not all possible implementations, and are not intended to limit the scope of the present disclosure. Corresponding reference numerals indicate corresponding parts throughout the several views of the drawings.

DETAILED DESCRIPTION

Embodiments of the present disclosure will now be described in further detail with reference to the accompanying drawings in order to enable those skilled in the art to practice with reference to the teachings.

As shown in FIG. 1, the radiotherapy system in this embodiment is a boron neutron capture therapy system 100, which includes a neutron generating device 10, a beam shaping assembly 20, a collimator 30, and a treatment table 40. The neutron generating device 10 includes an accelerator 11 and a target T, and the accelerator 11 accelerates charged particles (such as protons, deuterons, etc.) to generate a charged particle beam P such as a proton beam, and the charged particle beam P irradiates the target T and interacts with the target T to generate a neutron beam N, and the target T is a metal target. Suitable nuclear reactions are always determined according to such characteristics as desired neutron yield and energy, available accelerated charged particle energy and current and materialization of the metal target, among which the most discussed two are $^7$Li (p, n)$^7$Be and $^9$Be (p, n)$^9$B and both are endothermic reaction. Their energy thresholds are 1.881 MeV and 2.055 MeV respectively. Epithermal neutrons at a keV energy level are considered ideal neutron sources for BNCT. Theoretically, bombardment with lithium target using protons with energy slightly higher than the thresholds may produce neutrons relatively low in energy, so the neutrons may be used clinically without many moderations. However, Li (lithium) and Be (beryllium) and protons of threshold energy exhibit not high action cross section. In order to produce sufficient neutron fluxes, high-energy protons are usually selected to trigger the nuclear reactions. The target, considered perfect, is supposed to have the advantages of high neutron yield, a produced neutron energy distribution near the epithermal neutron energy range (see details thereinafter), little strong-penetration radiation, safety, low cost, easy accessibility, high temperature resistance etc. But in reality, no nuclear reactions may satisfy all requests. The target in these embodiments of the present disclosure is made of lithium. However, well known by those skilled in the art, the target materials may be made of other metals besides lithium or beryllium, for example, tantalum (Ta) or tungsten (W). The target T may be in the shape of a disk, or may be in other solid shapes, or a liquid (liquid metal) may be used. The accelerator 11 may be a linear accelerator, a cyclotron, a synchrotron, a synchrocyclotron, and the neutron generating device 10 may also be a nuclear reactor without using an accelerator and a target. No matter BNCT neutron sources are from the nuclear reactor or the nuclear reactions between the accelerator charged particles and the target, only mixed radiation fields are produced, that is, beams include neutrons and photons having energies from low to high. As for BNCT of deep tumors, except the epithermal neutrons, the more the residual quantity of radiation ray is, the higher the proportion of nonselective dose deposition in the normal tissue is. Therefore, radiation causing unnecessary dose should be lowered down as much as possible. In addition, for the normal tissues of the irradiated subject, too much various radiations should be avoided, which also causes unnecessary dose deposition.

The neutron beam N generated by the neutron generating device 10 sequentially passes through the beam shaping assembly 20 and the collimator 30 and then irradiates to the patient 200 on the treatment table 40. The beam shaping assembly 20 is capable of adjusting the beam quality of the neutron beam N generated by the neutron generating device 10, and the collimator 30 is used to concentrate the neutron beam N, so that the neutron beam N has higher targeting during the treatment process. By adjusting the collimator 30, the direction of the beam and the positional relationship of the beam and the patient 200 on the treatment table 40 can be adjusted, and the position of the treatment table 40 and the patient 200 can also be adjusted to align the beam with the tumor cells M in the patient 200. These adjustments can be performed manually or automatically through a series of control mechanisms. It will be appreciated that the present disclosure may also be provided without a collimator, and the beam from the beam shaping assembly 20 directly irradiates to the patient 200 on the treatment table 40.

The beam shaping assembly 20 further includes a reflector 21, a moderator 22, a thermal neutron absorber 23, a radiation shield 24, and a beam exit 25. The neutrons generated by the neutron generating device 10 have a wide spectrum of energy, and in addition to epithermal neutrons to meet treatment needs, it is desirable to reduce other types of neutrons and photons as much as possible to avoid injury to operators or patients. Therefore, the neutrons coming out of the neutron generating device 10 need to pass through the moderator 22 to adjust the energy of fast neutrons therein to the epithermal neutron energy region. The moderator 22 is made of a material having a cross section for principally acting with fast neutrons but hardly acting with epithermal neutrons. In this embodiment, the moderator 13 is made of at least one of $D_2O$, $AlF_3$, Fluental, $CaF_2$, $Li_2CO_3$, $MgF_2$ and $Al_2O_3$. The reflector 21 surrounds the moderator 22, and reflects the neutrons diffused through the moderator 22 back to the neutron beam N to improve the utilization of the neutrons, and is made of a material having high neutron reflection ability. In this embodiment, the reflector 21 is made of at least one of Pb or Ni. A thermal neutron absorber 23, which is made of a material having a large cross section for acting with thermal neutrons, is at the rear of the moderator 22. In this embodiment, the thermal neutron absorber 23 is made of Li-6. The thermal neutron absorber 23 is used to absorb the thermal neutrons passing through the moderator 22 to reduce the content of thermal neutrons in the neutron beam N, thereby avoiding overdosing in superficial normal tissues during treatment. A radiation shield 24 is disposed at the rear of the reflector around the beam exit 25 for shielding neutrons and photons that leak from portions other than the beam exit 25. The material of the radiation shield 24 includes at least one of a photon shielding material and a neutron shielding material. In this embodiment, the material of the radiation shield 24 includes a photon shielding material lead (Pb) and a neutron shielding material polyethylene (PE). The collimator 30 is disposed at the rear of the beam exit 25, and the epithermal neutron beam emerging from the collimator 30 irradiates to the patient 200, and is slowed into thermal neutrons to reach the tumor cell M after passing through the superficial normal tissue. It will be appreciated that the beam shaping assembly 20 may have other configurations as long as the epithermal neutron beam required for treatment can be obtained.

After the patient 200 is administrated or injected boron (B-10)-containing pharmaceuticals, the boron-containing pharmaceuticals selectively accumulates in the tumor cell M, and then takes advantage that the boron (B-10)-containing pharmaceuticals have high neutron capture cross section and produces $^4$He and $^7$Li heavy charged particles through $^{10}B(n,\alpha)^7Li$ neutron capture and nuclear fission reaction. The two charged particles, with average energy at about 2.33 MeV, are of high linear energy transfer (LET) and short-range characteristics. LET and range of the alpha particle are 150 keV/micrometer and 8 micrometers respectively while those of the heavy charged particle $^7$Li are 175 keV/micrometer and 5 micrometers respectively, and the total range of the two particles approximately amounts to a cell size. Therefore, radiation damage to living organisms may be restricted at the cells' level. only the tumor cells will be destroyed on the premise of having no major normal tissue damage.

The boron neutron capture therapy system 100 further includes a radiation shielding device 50. Although it is mainly the therapeutic epithermal neutron beam that irradiates to the patient 200 after passing through the beam shaping assembly 20 and the collimator 30 in the neutron beam N generated by the neutron generating device 10, in fact, it is still difficult to completely avoid other neutrons and photons mixed in, and these radiations may cause damage when irradiates to the normal tissues of the patient 200. In addition, although the therapeutic epithermal neutron beam has little influence on the normal human tissues, the possibility of causing dose accumulation still need to be further reduced, and therefore it is necessary to provide a radiation shielding device 50 to shield the portion of the patient that is not required to be irradiated by the beam for protection.

The radiation shielding device 50 further includes a medical image scanning means 51, a data processing and three-dimensional modeling means 52, and a shield 53. The medical image scanning means 51 scans an irradiated site of the patient 200 and outputs medical image voxel data. The irradiated site is defined as the coincident portion of a patient's body with a three-dimensional space formed by taking a certain irradiation depth from the end face of the irradiation apparatus (composed of the neutron generating device 10, the beam shaping assembly 20, and the collimator 30) close to the treatment table 40 in the irradiation direction, and taking a certain irradiation plane perpendicular to the irradiation direction. The medical image data may be data from Magnetic Resonance Imaging (MRI), Computed Tomography (CT), Positron Emission Tomography (PET), PET-CT or X-ray imaging. The following examples will be set forth based on data from computed tomography (CT), and the file format of CT is usually DICOM. However, well known by those skilled in the art, other medical image data, as long as being converted into a three-dimensional phantom tissue model, can be applied to the medical image-based radiation shielding device and method disclosed in the present disclosure.

After the patient 200 is positioned on the treatment table 40, the irradiated site of the patient 200 is scanned by CT to form a CT data file, that is, the medical image voxel data. The data processing and three-dimensional modeling means 52 establishes a three-dimensional phantom tissue model based on the medical image voxel data, for example, 3D visualization is conducted by using 3D modeling software such as MI-3DVS software or CAD software. The three-dimensional phantom tissue model includes diseased tissues and normal tissues. According to the three-dimensional phantom tissue model, a three-dimensional shield model for normal tissues is established, and the installation position of the shield is determined. The three-dimensional shield model can be combined with data information of the irradiation apparatus, such as beam intensity, beam flux, beam diameter, irradiation path, etc., and positional relationship between the irradiation apparatus and the irradiated site. In this process, artificial corrections can also be made based on actual conditions. It can be understood that the CT scan can also be performed before the patient 200 enters the treatment room, so that the medical image scanning means 51 does not need to be integrated into the treatment room, and the CT data file of the irradiated site determined by scanning using the existing CT scanner of the hospital is available. At this time, the data information of the irradiation apparatus, such as the beam intensity, the beam flux, the beam diameter, the irradiation path, and the like, and the positional relationship between the irradiation apparatus and the irradiated site are also determined in accordance with the irradiated site determined by the scanning, and then the three-dimensional shield model is established based on the above data information.

The shield 53 is formed by printing with a 3D printer, data of the three-dimensional shield model is inputted into the 3D printer. The STL format file for recording the 3D model data is input into the computer system, and layered into two-dimensional slice data, and layer-by-layer printing is performed by a computer-controlled 3D printing system, and the three-dimensional product is finally obtained after being superimposed. The shield 53 can shield the normal tissues of the patient 200 from the radiation generated by the irradiation apparatus, and the beam passes through the shield 53 and then acts on the tumor cells M of the patient 200 on the treatment table 40. The shield 53 is located between the irradiation apparatus and the irradiated site, and in this embodiment, the shield is located between the collimator or the beam exit and the irradiated site. The material of the shield 53 includes at least one of a material for shielding neutrons or a material for shielding photons. In this embodiment, the shield 53 has a plate shape and is directly fixed to the body surface of the patient's irradiated site, and is matched with the body surface shape of the site of patient to be mounted, and is easy to be correctly installed. The fixing manner may be adhesion, a strap or a buckle. The shield 53 has a central through hole 531, and the ratio of the diameter of the central through hole 531 to the maximum size of the tumor cell M in the patient 200 in a direction perpendicular to the beam direction is 1-2. While killing tumor cells, the damage of normal tissues is minimized. In this embodiment, the shape of the central through hole 531 is an outer contour shape of the projection of the tumor cell M parallel to the beam direction, and the diameter defined by the central through hole can be understood as the diameter of the outer contour shape. It can be understood that the shield 53 may not have a central through hole, but may have a different thickness in the central portion from the other portions or the entire shield may have different thicknesses at different positions. The maximum thickness of the shield 53 ranges from 3 to 20 mm, and the outer surface has an area ranging from 10 to 200 $cm^2$. Due to the use of 3D printing, the shield 53 can be respectively formed according to individual differences of different irradiated subjects, and can rapidly model complex shapes, and a better radiation shielding effect can be obtained. In some special-shaped parts, the shield 53 may also be plural to facilitate installation. The shield 53 may also be fixed to the treatment table or collimator or beam exit. It is also possible to combine the 3D printer with the treatment table or the collimator or the beam exit to determine the mutual positional relationship and print the shield directly at the corresponding position. By scanning the patient's tumor site with medical images, a targeted 3D printed shield is obtained, and the proportion of radiation that is attenuated after passing through the shield can be ≥50%, and is ≥80% in this embodiment. The patient's normal tissues receive a radiation dose of less than 18 Gy during the boron neutron capture therapy. The ratio of radiation depth to the normal tissues of the radiation when passing through the shield compared to when not passing through is ≤50%. The material, shape, and structure of the shield 53 may be designed to be more complex, and the path of the neutron beam from the collimator or the beam exit can be changed to match the three-dimensional shape of the tumor cells, such as the center through hole 531 is composed of different line segments in the beam direction, and different portions of the shield body 53 are composed of different materials.

The medical image-based radiation shielding method of this embodiment includes the following steps:

S1: a medical image scanning means 51 scans an irradiated site of the patient 200 and outputs medical image voxel data of the irradiated site;

S2: a data processing and three-dimensional modeling means 52 establishes a three-dimensional phantom tissue model according to the medical image voxel data obtained by S1;

S3: the data processing and three-dimensional modeling means 52 establishes a three-dimensional shield model according to data of the three-dimensional phantom tissue model obtained by S2;

S4: data of the three-dimensional shield model is inputted into a 3D printer to print a shield 53;

S5: the shield 53 is installed and positioned.

Step S3 further includes collecting or inputting data information of the irradiation apparatus, such as beam intensity, beam flux, beam diameter, irradiation path, etc., and positional relationship between the irradiation apparatus and the irradiated site, and then establishing the three-dimensional shield model in combination with the data of the three-dimensional phantom tissue model, and determining the shield location. In this process, artificial correction can also be made according to the actual situation.

In the embodiment of the present disclosure, the medical image scanning means can be used to obtain the tissue structure of the irradiated site of the patient, thereby obtaining the shield in a targeted manner according to the shape, position, size, and the like of the tumor cell. It can be understood that the present disclosure can also adopt a non-medical image scanning means, such as a three-dimensional image scanning means that scans only the shape of the patient's body surface, thus obtaining three-dimensional data of the shape of the patients for three-dimensional modeling, thereby obtaining a 3D printed shield that matches the shape of the irradiated site.

It will be appreciated that the present disclosure is also applicable to other fields of radiotherapy well known to those skilled in the art that require irradiation to diseased tissue while protecting normal tissues from irradiation or in less irradiation. The neutron generating device is accordingly replaced with other radiation generating device such as a proton generating device, a heavy ion generating device, an X-ray generating device or a gamma ray generating device. It can also be applied to other diseases that can be treated with radiation, such as Alzheimer's disease, rheumatoid arthritis, and tumor cells are other diseased tissues accordingly. The irradiated subject in the present embodiment is a cancer patient, and it can be understood that the irradiated subject may be other organism such as a mammal.

The positional relationship in the embodiment of the present disclosure refers to the positional relationship along the direction of the beam transport path, and the "rear" refers to the downstream of the beam direction.

Although the illustrative embodiments of the present invention have been described above in order to enable those skilled in the art to understand the present invention, it should be understood that the present invention is not to be limited the scope of the embodiments. For those skilled in the art, as long as various changes are within the spirit and scope as defined in the present invention and the appended claims, these changes are obvious and within the scope of protection claimed by the present invention.

What is claimed is:

1. A medical image-based radiation shielding device for shielding normal tissues of an irradiated subject from radiation of an irradiation apparatus in a radiotherapy system, comprising:
   a medical image scanning means for scanning an irradiated site of the irradiated subject and outputting medical image voxel data;
   a data processing and three-dimensional modeling means for establishing a three-dimensional phantom tissue model according to the medical image voxel data and establishing a three-dimensional shield model according to the three-dimensional phantom tissue model;
   a shield configured to be located between the irradiation apparatus and the irradiated site, wherein the shield is formed by printing the three-dimensional shield model data input to a 3D printer;
   wherein the radiotherapy system is a boron neutron capture therapy system, the irradiated subject is a cancer patient, and the irradiation apparatus comprises a radiation generating device; and wherein the radiation generating device is a neutron generating device comprising an accelerator and a target, and the accelerator accelerates charged particles to interact with the target to generate neutrons.

2. The medical image-based radiation shielding device according to claim 1, wherein the three-dimensional shield model is established according to the three-dimensional phantom tissue model, combined with data information of the irradiation apparatus and positional relationship between the irradiation apparatus and the irradiated site.

3. The medical image-based radiation shielding device according to claim 1, wherein a material of the shield comprises at least one of a material for shielding neutrons and a material for shielding photons, and the shield is configured to be fixed on a surface of the irradiated subject to match surface shape of the irradiated subject.

4. The medical image-based radiation shielding device according to claim 3, wherein the shield comprises a central through hole, and a ratio of a diameter of the central through hole to a maximum size of internal diseased tissues of the irradiated subject in a direction perpendicular to a beam direction is 1-2, and a maximum thickness of the shield ranges from 3 to 20 mm, and an area of an outer surface of the shield is in the range from 10 to 200 cm$^2$.

5. The medical image-based radiation shielding device according to claim 1, wherein radiation generated by the irradiation apparatus is attenuated by the shield by $\geq 50\%$, and a ratio of radiation depth to normal tissues of the radiation when passing through the shield compared to when not passing through is $\leq 50\%$.

6. A radiotherapy system comprising:
   an irradiation apparatus for irradiating an irradiated subject to form an irradiated site, wherein the radiotherapy system is a boron neutron capture therapy system, the irradiated subject is a cancer patient, and the irradiation apparatus comprises a radiation generating device, wherein the radiation generating device is a neutron generating device comprising an accelerator and a target, and the accelerator accelerates charged particles to interact with the target to generate neutrons; and
   a shield configured to be located between the irradiation apparatus and the irradiated site, wherein the shield is formed by printing with a 3D printer.

7. The radiotherapy system according to claim 6, wherein the radiotherapy system further comprises a three-dimensional image scanning means and a data processing and three-dimensional modeling means, wherein the three-dimensional image scanning means scans the irradiated site and outputs three-dimensional data; the data processing and three-dimensional modeling means establishes a three-dimensional model of the irradiated site according to the three-dimensional data, and establishes a three-dimensional shield model according to the three-dimensional model of the irradiated site; the shield is formed by printing with a 3D printer, data of the three-dimensional shield model is inputted into the 3D printer.

8. The radiotherapy system according to claim 6, wherein the radiotherapy system further comprises a medical image scanning means and a data processing and three-dimensional modeling means, wherein the medical image scanning means scans the irradiated site and outputs medical image voxel data; the data processing and three-dimensional modeling means establishes a three-dimensional phantom tissue model according to the medical image voxel data, and establishes a three-dimensional shield model according to the three-dimensional phantom tissue model; the shield is formed by printing with a 3D printer, data of the three-dimensional shield model is inputted into the 3D printer.

9. The radiotherapy system according to claim 8, wherein the irradiation apparatus further comprises a beam shaping assembly, and a collimator, wherein the radiation generating device is capable of generating radiation, the beam shaping assembly is capable of adjusting beam quality of the radiation generated by the radiation generating device and includes a beam exit, the collimator is capable of concentrating radiation passing through the beam shaping assembly, and the shield is configured to be located between the collimator or beam exit and the irradiated site.

10. The radiotherapy system according to claim 9, wherein the radiotherapy system further comprises a treatment table, wherein the radiation passes through the shield and acts on diseased tissues of the patient on the treatment table, the shield is configured to be fixed on a surface of the irradiated subject or to the treatment table or the collimator or the beam exit.

11. The radiotherapy system according to claim 6, wherein normal tissues of the patient receive a radiation dose of less than 18 Gy during a boron neutron capture therapy performed by the radiotherapy system.

12. A medical image-based radiation shielding method for shielding an irradiated subject from radiation of an irradiation apparatus in a radiotherapy system, comprising the steps of:
scanning an irradiated site of an irradiated subject by a medical image scanning means, and outputting medical image voxel data of the irradiated site;
establishing a three-dimensional phantom tissue model according to the medical image voxel data;
establishing a three-dimensional shield model according to data of the three-dimensional phantom tissue model;
inputting data of the three-dimensional shield model into a 3D printer to print a shield; and
installing and positioning the shield;
wherein the radiotherapy system is a boron neutron capture therapy system, the irradiated subject is a cancer patient, and the irradiation apparatus comprises a radiation generating device; and wherein the radiation generating device is a neutron generating device comprising an accelerator and a target, and the accelerator accelerates charged particles to interact with the target to generate neutrons.

13. The medical image-based radiation shielding method according to claim 12, wherein the step of establishing a three-dimensional shield model according to data of the three-dimensional phantom tissue model further comprises collecting or inputting data information of the irradiation apparatus and positional relationship between the irradiation apparatus and the irradiated site, and establishing the three-dimensional shield model in combination with the data of the three-dimensional phantom tissue model, and determining shield location.

* * * * *